United States Patent [19]
Taylor et al.

[11] Patent Number: 5,504,572
[45] Date of Patent: Apr. 2, 1996

[54] ELECTRONIC IMAGING APPARATUS FOR DETERMINING THE PRESENCE OF STRUCTURE WITHIN OPAQUE OBJECTS AND METHODS OF MAKING THE SAME

[76] Inventors: Mark A. Taylor, 2575 N. Farm Rd. 93; John L. Williams, Rte. 4, Box 814, both of Springfield, Mo. 65802

[21] Appl. No.: 266,985

[22] Filed: Jun. 28, 1994

[51] Int. Cl.$^6$ .................................................. G01N 33/08
[52] U.S. Cl. ............................................................ 356/53
[58] Field of Search ............................................... 356/53

[56] References Cited

U.S. PATENT DOCUMENTS

| | | |
|---|---|---|
| 752,806 | 2/1904 | Southworth . |
| 808,117 | 12/1905 | Shoemaker . |
| 1,229,936 | 6/1917 | Gilpin . |
| 1,236,080 | 8/1917 | Hickman . |
| 3,540,824 | 11/1970 | Fonda et al. ............ 356/53 |
| 4,063,823 | 12/1977 | Graf ....................... 356/240 |
| 4,268,168 | 5/1981 | Dawaele ................. 356/58 |
| 4,671,652 | 6/1987 | van Asselt et al. ...... 356/66 |
| 4,767,928 | 8/1988 | Nelson et al. .......... 250/341 |
| 4,788,427 | 11/1988 | LeRoy ................... 250/330 |
| 4,978,225 | 12/1990 | Reimer .................. 366/53 |
| 5,085,511 | 2/1992 | Grisel ..................... 356/239 |
| 5,321,491 | 6/1994 | Summers et al. ........ 356/53 |

FOREIGN PATENT DOCUMENTS

| | | |
|---|---|---|
| 1049578 | 12/1953 | France . |
| 211544 | 9/1987 | Japan ..................... 356/53 |

OTHER PUBLICATIONS

Emu Today & Tomorrow vol. 4, Issue 4, Apr. 1994 pp. 1,2 & 120.
INNER–VISION PRO–850 (undated) 5 pages.
Several Important Reasons to Candle Your Emu Eggs(undated) 12 pages With the Inner–Vision Pro–850 Emu Egg Candling System.

*Primary Examiner*—Richard A. Rosenberger
*Attorney, Agent, or Firm*—Richard L. Marsh

[57] ABSTRACT

An electronic imaging apparatus is provided which has means for detecting the presence of internal structure in an opaque or translucent object. The apparatus has a light source directing a beam of light towards the object from one side and a light receiver on another side thereof to convert invisible light passing through the object into a visible image. Means to record the image produced is made available as well as means to produce a three dimensional image or drawing.

39 Claims, 4 Drawing Sheets

ELECTRONIC IMAGING APPARATUS FOR DETERMINING THE PRESENCE OF STRUCTURE WITHIN OPAQUE OBJECTS AND METHODS OF MAKING THE SAME

BACKGROUND OF THE INVENTION

1. Field of the Invention

This invention relates to a novel apparatus for detecting the presence of or determining or defining the shape of internal structure in an opaque or translucent object, methods of using the apparatus and methods of making the novel apparatus.

2. Prior Art Statement

The successful farming of birds is dependent upon many factors but the primary harvest of fertilized eggs and the successful incubation of those eggs determines the size of the farmer's flock. Most birds have egg shells that permit visible light to pass through the egg shell and the determination of a fertilized egg or a rotten egg can be determined by placing the egg before a light source such as a candle, hence the term "candling of eggs". Candling, however, permits only the simple act of determining if the egg is fertilized or rotten and little if any internal structure can be observed although the position of the air sac may sometimes be determined. Such a technique is usable only on translucent shells. Webster's Third New International Dictionary of the English Language (unabridged) defines opaque as "impervious to the rays of visible light" and translucent as "admitting and diffusing light so that objects beyond cannot be clearly distinguished." In these contexts, Webster's clearly refers to visible light, that portion of the light spectrum which is distinguishable by the human eye as contrasted to the invisible infrared or ultraviolet portions of the light spectrum.

Some bird eggs cannot be candied utilizing visible light. For instance, emu and cassowary eggs cannot be candied as the very dark green emu egg shells or the dark green spots on cassowary egg shells do not pass the portion of the white light spectrum that is visible to the human eye. An emu egg is therefore opaque to visible light and conventional techniques cannot be employed Therefore, it is impossible to determine if an emu egg is fertilized or rotten and disastrous results, such as an exploding rotten egg in the incubation chamber, are possible. The emu farmer has, therefore, relied upon tried and true methods of hatching other eggs and determined causes of poor hatch rates by careful documentation of all incubated emu eggs. Consequently, individuals desiring to hatch emu eggs are not as successful due to the inability to determine egg fertility, chick position, air cell size, location and embryonic development.

In the case of other ratites, some individuals are unable to candle these eggs effectively enough to determine chick position, and/or embryonic development and are desirous of a method and apparatus to enhance the hatch rate of these otherwise translucent eggs. Furthermore, the conventional poultry farmer could benefit from an enhanced method and apparatus of detecting the presence of fertilization or determining and defining the internal structure of these otherwise translucent bird eggs.

It is known to construct an egg tester to determine if translucent eggs are fresh by providing means to pass visible light through the eggs and observe the light reflected upon a mirror disposed below the eggs. For example, see the U.S. Pat. No. 752,806, issued on Feb. 23, 1904, to Preston B. Southworth.

It is known to provide a lamp as a visible light source disposed within a container having egg openings on the top thereof to determine the freshness of translucent eggs. For instance, see U.S. Pat. No. 808,117, issued on Dec. 26, 1905 to Jacob S. Shoemaker.

It is known to provide an incandescent lamp as a light source disposed within a container having egg openings on the top thereof to determine the freshness of translucent eggs. For instance, see U.S. Pat. No. 1,229,936, issued on Jun. 12, 1917 to Robert W. Gilpin or U.S. Pat. No. 1,236,080, issued on Aug. 7, 1917 to Henry Hickman.

It is further known to provide a luminescent light source disposed within a container having egg openings on the top thereof to determine the freshness of translucent eggs. For instance, see French Patent No. 1,049,578, issued on Aug. 19, 1953 to M. Pierre-Onofre Calafat.

It is also known to provide multiple reflectors mounted in each lane of a conveyor to direct light to each lane for the purpose of candling translucent eggs. For instance, see U.S. Pat. No. 4,268,168, issued on May 19, 1981 to Daniel C. C. Dewaele.

It is also known to provide a light source and a light sensor arranged in such an array that the translucent articles to be candied are shielded relative to each other. For instance, see U.S. Pat. No. 4,671,652, issued on Jun. 9, 1987 to Peter A. van Asselt, et al.

It is known to provide a method of detecting whether an egg is fertilized or diseased using a thermograph scanner to give a visual indication of a heat pattern emanating from an egg and comparing the visual indication with a known reference heat pattern. For instance, see the U.S. Pat. 4,788,427, issued on Nov. 29, 1988 to Pierre L. LeRoy.

Finally it is known to use an electric light source for visually inspecting a shotgun shell for the desired arrangement of powder, wad, and shot of a loaded shotgun shell and having means for transmitting a video signal to a remotely placed television set for viewing the image of each shell. For instance, see U.S. Pat. No. 5,085,511, issued on Feb. 4, 1992 to Howard L. Grisel.

SUMMARY OF THE INVENTION

It is an object of this invention to provide an electronic imaging apparatus having means for detecting the presence of internal structure in an opaque or translucent object, wherein the apparatus has a light source directing a beam of light towards the object from one side and a receiver on another side thereof to convert invisible light passing through the object into a visible image.

It is another object of this invention to provide an imaging apparatus having means for determining the shape of the internal structure in an opaque or translucent object, wherein the apparatus has a light source directing a beam of light towards the object from one side and a receiver on another side thereof to convert invisible light passing through the object into a visible image.

It is another object of this invention to provide an imaging apparatus having means for defining the shape of the internal structure in an opaque or translucent object, wherein the apparatus has a light source directing a beam of light towards an object from one side and a receiver on another side thereof to convert invisible light passing through the object into a visible image.

It is another object of this invention to provide an imaging apparatus having means for defining the shape of the internal structure in an opaque or translucent object, wherein the apparatus has a light source directing a beam of light towards an object from one side and a receiver on another side thereof to convert invisible light passing through the object and timer having means transmitting the image derived to a remote location.

It is another object of this invention to provide an imaging apparatus having means for defining the shape of the internal structure in an opaque or translucent object, wherein the apparatus has a light source directing a beam of light towards an object from one side and a receiver on another side thereof to convert invisible light passing through the object and recording the image derived for delayed viewing or for storage and retrieval for research and/or archival purposes.

It is another object of this invention to provide means to indicate the presence of fertilization in a ratite egg.

It is another object of this invention to provide means to indicate the presence of fertilization in an avian ovum.

It is another object of this invention to provide means to view chick position and orientation within a fertilized ratite egg.

It is another object of this invention to provide means to view chick position and orientation within a fertilized an avian ovum.

It is another object of this invention to provide means to view chick position and orientation within a fertilized ratite egg while manipulating the embryo to improve chick hatching.

It is another object of this invention to provide means to view chick position and orientation within a fertilized an avian ovum while manipulating the embryo to improve chick hatching.

It is another object of this invention to provide means to view chick position and orientation within a fertilized ratite egg while performing surgery on the embryo to improve chick hatching.

It is another object of this invention to provide means to view chick position and orientation within a fertilized an avian ovum while performing surgery on the embryo to improve chick hatching.

It is still another object of this invention to provide means to rotate the opaque object in order to develop an multidimensional image which may be viewed from different perspectives to accomplish the improved results.

It is yet another object of this invention to provide an imaging apparatus having means for defining the shape of the internal structure in an opaque or translucent object, wherein the apparatus has at least one light source directing a beam of light towards an object from one side and multiple receivers disposed on other sides thereof to convert invisible light passing through the object into a visible image.

It is yet another object of this invention to provide a method of making an electronic imaging apparatus having means for detecting the presence of or defining the internal structure in an opaque or translucent object, wherein the apparatus has a light source directing a beam of light towards the object from one side and a receiver on another side thereof to convert invisible light passing through the object into a visible image.

Other objects and uses of the apparatus of this invention will become apparent through a careful reading of the specification and careful attention to the drawings appended herewith.

DESCRIPTION OF THE PREFERRED EMBODIMENTS

Figure 1:
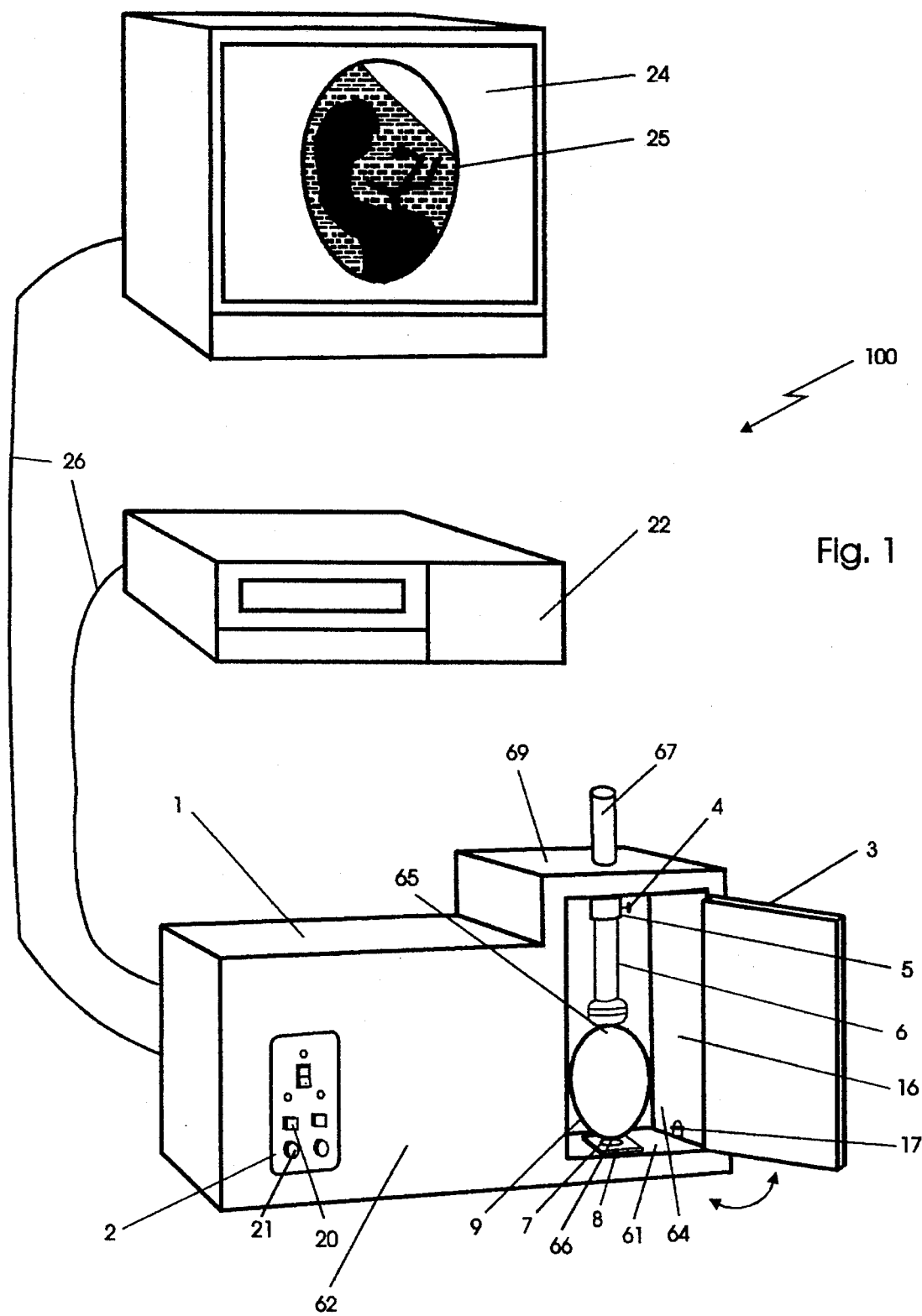
FIG. 1 is a perspective view of an embodiment of an electronic imaging apparatus showing a separate viewing device, a separate recording device and an opaque object in a compartment of the apparatus with a closure door in the open position.

While the various features of this invention are hereinafter described and illustrated as an electronic imaging apparatus primarily intended for the viewing of ratite eggs, more specifically for emu eggs, the apparatus using a charge coupled device to capture an image of the contents of the egg, convert the electronic signal to a visible means and display same on a video monitor and/or to record same upon video recording media, it is to be understood that the various features of this invention can be utilized singly or in any combination thereof to provide an imaging apparatus for other opaque or translucent objects as desired.

Therefore, this invention is not to be limited to only the embodiments illustrated in the drawings, or described in the following specification and claims because the drawings are merely utilized to illustrate one of the wide variety of uses of this invention.

In the raising of birds, particularly retires, where birds are kept by farmers and eggs are harvested for incubation and hatching, and in an attempt to increase their flock population, it has been determined that the ratite hatch rate is not as high as desired. The emu's dark colored egg, which does not pass white light, cannot be candied leaving the farmer with considerable doubt as to the fertility of his eggs. Furthermore, the bird farmer in general has no means of closely monitoring embryonic development.

An electronic imaging apparatus has therefore been designed to facilitate the examination of the internal structure of opaque or translucent objects and is especially useful in detecting the presence of fertilization and tracking the embryonic development of emu eggs. This apparatus provides a composite video signal enabling the contents of the opaque or translucent object to be displayed on a video monitor, and via a video recorder, allows the recording of the image of internal structure of the object onto video tape. Incorporated in this apparatus is a compartment, whereby a single object may be placed in a holding device that allows rotation by the user. Once in the compartment, the object is in the path of an electronic image sensor allowing the object to be scanned by the electronic image sensor which then converts the image of the internal structure of the object into an electronic video signal. This compartment completely shields the object from all external light, thus allowing the observer to examine the object in a lighted room.

Referring specifically to FIG. 1, the electronic imaging apparatus generally indicated by the FIG. 100, is comprised of a housing 1 having an integral enclosure or compartment 16, in which an opaque or translucent object 9, such as an emu egg, to be inspected is placed. Apparatus 100 has a door 3, which when closed on compartment 16, completely shields object 9 from any and all external light. Object 9 rests on a rubber base grommet 7, which in turn rests on a bearing or rotatable element 8 that allows rotation of object 9. Rotatable element 8 is shown resting on bottom 61 of compartment 16, but of course may be mounted upon a vertically moveable structure within compartment 16 to enable object 9 to be viewed at various heights without moving invisible light receiving means 10 hereinafter described.

Apparatus 100 has a light source assembly such as light emitting means 6 comprised of a tube, focusing reflector, incandescent lamp, power button, these internal parts not shown for simplicity, inserted into a holder 5, slightly larger in diameter than the aforementioned light emitting means 6. Although light emitting means 6 preferably comprises an incandescent lamp, an invisible light emitting lamp could also be used emitting only infrared or ultraviolet light. Holder 5 is installed into an opening in top 69 of compartment 16 so as to be centered in compartment 16 and extending down from top 69 no more than one haft the length of fight emitting means 6. Holder 5 does not normally protrude above top 69 of compartment 16 such that unobstructed handling of light emitting means 6 is made possible. Light emitting means 6, when installed in holder 5, may be raised, lowered and/or rotated by the user or held in place by retaining means such as set screw 4 threaded into a hole in the lower portion of holder 5. Set screw 4 is so positioned that the user may tighten or loosen set screw 4 when placing object 9 upon base grommet 7, thereby allowing light emitting means 6 to either be locked in position or remain free of any hindrance to movement. Light emitting means 6 may be lowered onto top surface 65 of object 9, as object 9 is resting on base grommet 7, so as to provide a seal between object 9 and light emitting means 6 such that light does not enter or exit the area between light emitting means 6 and object 9.

Figure 3:
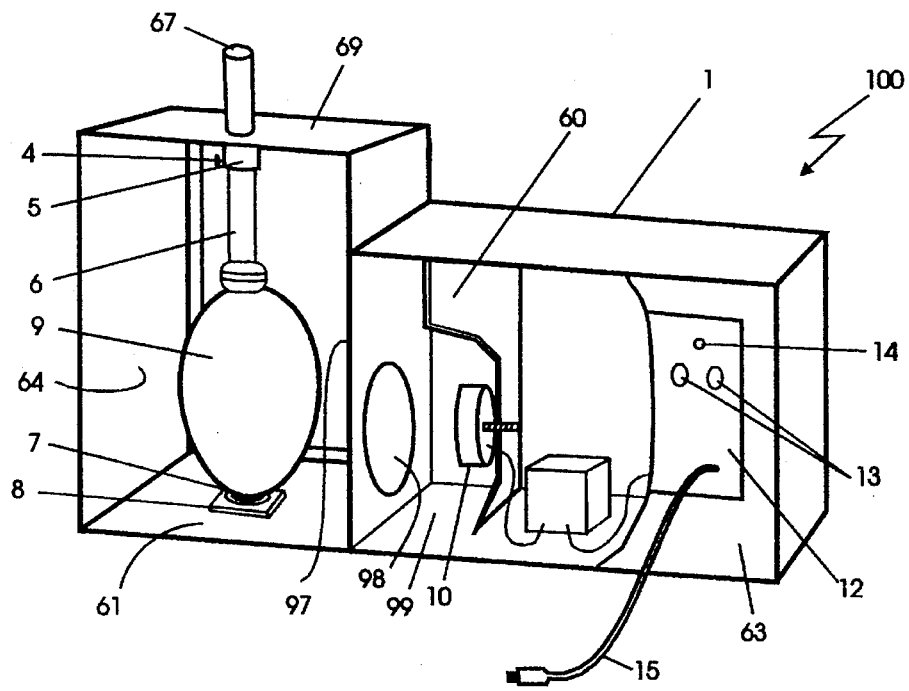
FIG. 3 is a rear perspective view with portions removed to show a light receiving means and associated electrical wiring.

Referring now to FIG. 3, object 9, when placed in compartment 16, is in the direct path of an electronic image sensor such as invisible light receiving means 10 adapted to determine the internal structure of object 9, and create an electronic video signal of the internal structure of object 9. The preferred embodiment of invisible light receiving means 10 comprises a charge coupled device such as the SFS VDC9212 charge coupled device manufactured by the SFS Corporation. The VDC9212 charge coupled device requires modification of the internal electrical circuitry as it employs the use of an invisible infrared light source intended for un-detected monitoring in an non-lighted environment. The invisible infrared light source contained in the VDC9212 must be disabled by removing the light emitting diodes that emit the invisible infrared fight. Other devices, such as the newvicon tube, manufactured by the Hitachi Corporation or the saticon tube, manufactured by the Matsushita Corporation may be employed, which, although each has the capability to convert invisible infrared light to an dectronic video signal, may not be of the desired quality to perform satisfactorily as invisible fight receiving means 10. Furthermore, the portable video taping device typically referred to as a "camcorder" may be utilized in this application as an invisible light receiving means 10, however, the auto-focus lens which uses infrared light to determine the distance between the subject to be video taped and the lens so that the lens may be focused on the subject must be similarly disabled and the camcorder's sensors which are shielded by an optical coating which will not pass invisible infrared light, must either be modified or replaced to accept the invisible light.

Figure 4:
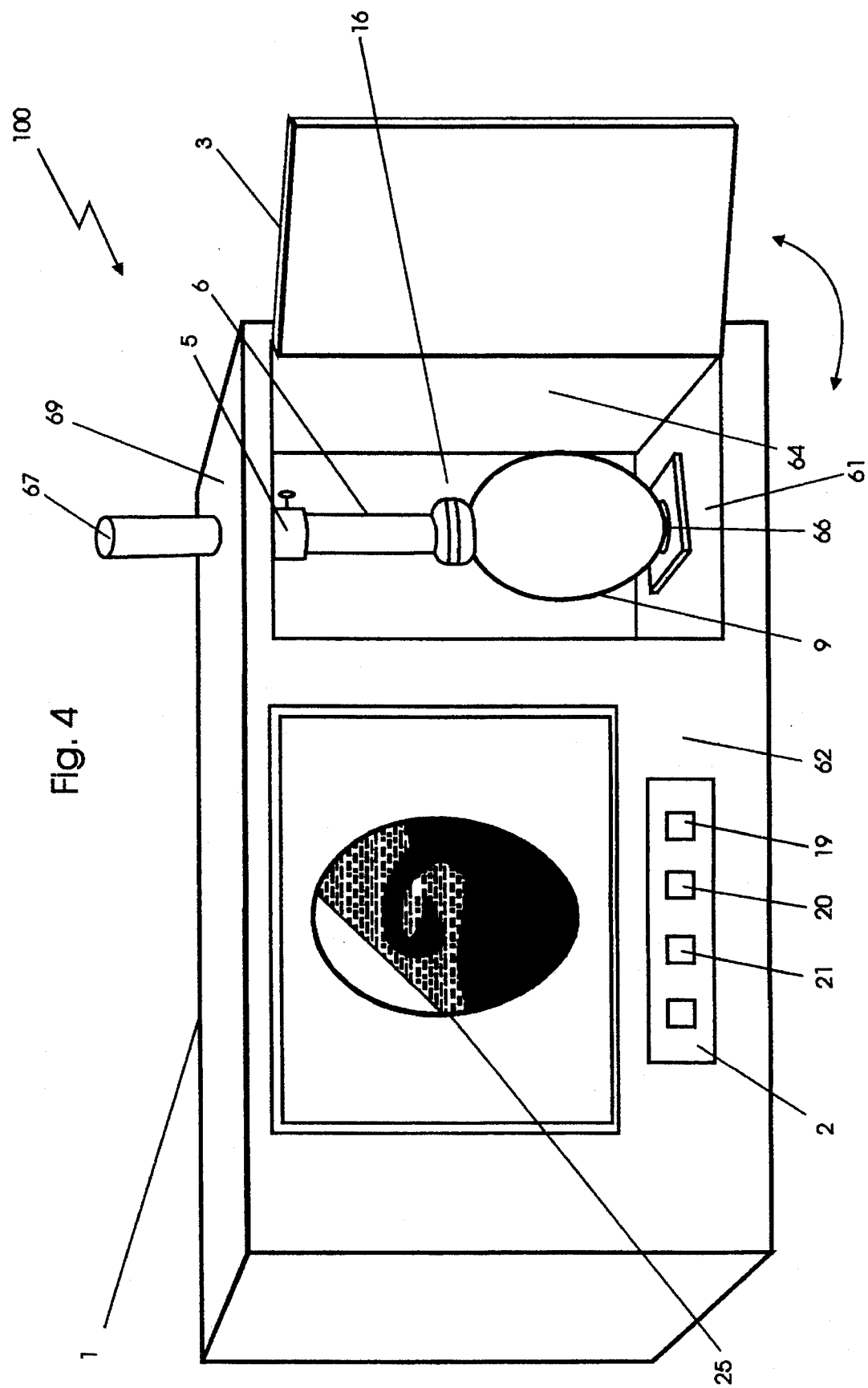
FIG. 4 is a perspective view of the preferred embodiment showing integral viewing device, an opaque object to be viewed and an image of the opaque object displayed on the viewing device.

Invisible light receiving means 10 is fixedly mounted in a wall 60 of a compartment 99 adjacent to compartment 16, and extends into compartment 99 but not into compartment 16 in apparatus 100 to protect invisible light receiving means 10 from damage. A viewing port 98 is provided in common wall 97 of compartment 16 and compartment 99 and is of such size as to accomplish viewing the entire shape of object 9. Invisible light receiving means 10 is coupled to an electronic monitor such as viewing device 24 which may be remote as shown in FIG. 1 or integral with apparatus 100 as shown in FIG. 4. Invisible light receiving means 10 may additionally be coupled to a video recording device 22 as further shown in FIG. 1.

As shown in FIG. 4, a control panel 2, is mounted on face 62 of apparatus 100. A main power switch 19, at least one lamp switch 20, and at least one dimmer switch 21 are mounted within control panel 2 and are adapted for easy access by the user of apparatus 100. FIG. 3 illustrates power supply panel 12 on back wall 63 of apparatus 100, power supply panel 12 having a power cord 15 adapted to receive electrical energy from an outside energy source, at least one fuse holder 13 and at least one video jack 14. Video jack 14 is adapted to connect apparatus 100 to remote viewing device 24 and/or recording device 22.

Compartment 16 may be lined with shock absorbing material (not shown) such as foam rubber. The shock absorbing material reduces the incidence of damage to object 9 in the event of accidental mishandling.

Figure 2:
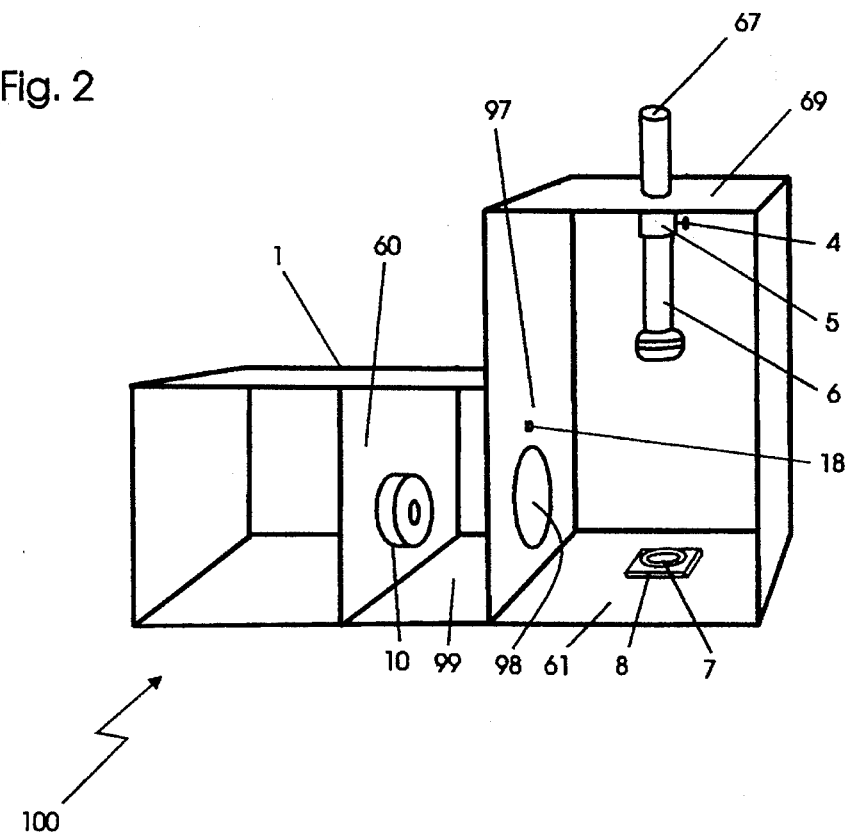
FIG. 2 is a perspective view with portions removed to show the separate compartments.

As best shown in FIGS. 1 and 2, compartment 16 may be illuminated by at least one small incandescent lamp, such as a front lamp 18 and/or a back lamp 17, with back lamp 17 placed in wall 64 opposite invisible light receiving means 10, with the position of object 9 disposed therebetween. Lamps 17 and/or 18 are used for the purpose of facilitating the placement of object 9 in compartment 16 and for observing and/or marking of a specific orientation of object 9 with respect to invisible light receiving means 10, but do not interfere with the viewing of image 25 of the internal structure of object 9 as invisible light receiving means 10 is shielded from lamp 17 by object 9. Front lamp 18 is placed on common wall 97 between invisible light receiving means 10 and object 9 thereby preventing light from lamp 18 from entering invisible light receiving means 10. Lamps 17 and 18 may be turned on by activating lamp switch 20 that supplies electric current to respective lamps 17 and/or 18, and the light produced by lamps 17 and/or 18 may be attenuated by rotating dimmer switch 21. lamp 18 may be replaced by an ultraviolet lamp generally used to reduce or eliminate bacteria or a separate lamp (not shown) may be installed for this purpose. Such an ultraviolet lamp is used to sterilize the surfaces or internal components as well the surfaces of object 9.

Referring again to FIG. 1, the preferred method of viewing the internal structure of an opaque or translucent object 9 will be illustrated. Object 9 is placed in compartment 16 of apparatus 100 upon grommet 7 which is disposed on rotatable element 8. Light emitting means 6 is placed directly on a top surface 65 of object 9 directly opposite bottom surface 66 resting on grommet 7. The weight of light emitting means 6 is sufficient to retain object 9 in a vertical position upon grommet 7. FIG. 3 shows invisible light receiving means 10 disposed in a position such that an unobstructed view of the entirety of object 9 intermediate grommet 7 and light emitting means 6 is made possible through viewing port 98. Door 3 of compartment 16 is then closed and may have latch means (not shown) interlocking the electrical and electronic circuits from accidental activation.

Main power switch 19 is activated which in turn activates invisible light receiving means 10. Separate switches, not shown, are used to supply power to light emitting means 6, viewing device 24 and recording device 22, but of course, light emitting means 6, viewing device 24, lamp switch 20, dimmer switch 21 and recording device 22 could all be interconnected with main power switch 19. When light emitting memos 6 is turned on, the light emitted therefrom passes into object 9 and any structure found within object 9 blocks the passage of light while the absence of structure permits that portion of object 9 to pass the remaining light to invisible light receiving means 10. If no structure is present in object 9, object 9 appears to invisible light receiving means 10 as a glowing object the same shape as object 9. If detectable structure is present, such as the fertilization of egg 11, invisible light receiving means 10 detects this beginning embryo 44 as a dark spot 42 (as best shown in FIG. 5B) and displays same as a two dimensional planar outline. Apparatus 100 may be fitted with at least one indicating lamp (not shown) on panel 2 with one such lamp labeled "Fertile" to indicate the presence of detectable structure. As the embryo 44 develops, the size and shape of the outline enlarges. The video signal generated by the invisible light receiving means 10 is transmitted via interconnecting cable 26 to viewing device 24 and/or recording device 22, whereby an image 25 of object 9 may be observed. While image 25 is appearing on viewing device 24, upper end 67 of light emitting means 6 may be rotated in either direction to enable the viewing of object 9 from another angle. When desired image 25 is observed on viewing device 24, recording device 22 may be activated to preserve image 25. Recording device 22 may, of course, be activated at all times in order to preserve images of each angle of view of object 9.

Apparatus 100 is particularly useful for conducting research to determine proper incubation procedures for eggs. Presently, empirically derived criteria based upon invasive procedures used to determine the time to turn, the presence or location of air sac 51, the yolk sac (not shown) sinking to bottom 43 or embryo 44 floating upwards to top of egg 11 have usually resulted in destruction of a number of eggs 11. Such invasive procedures are unnecessary as apparatus 100 may be used to provide a non-invasive measure or indication of these criteria in order to conduct more fruitful research. It may be found that the empirically derived criteria may not be entirely correct which may effect the hatch rate of embryos, and in particular emu embryos.

Figure 5:
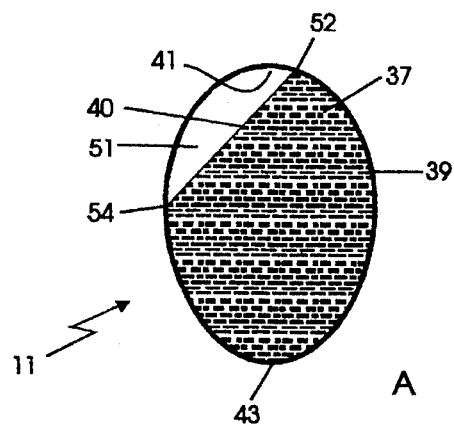
FIG. 5 is a series of images of an emu egg showing various stages of development of an embryo within the egg.
Figure 5:
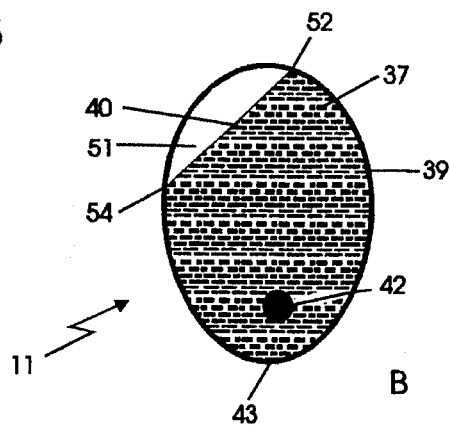
Figure 5:
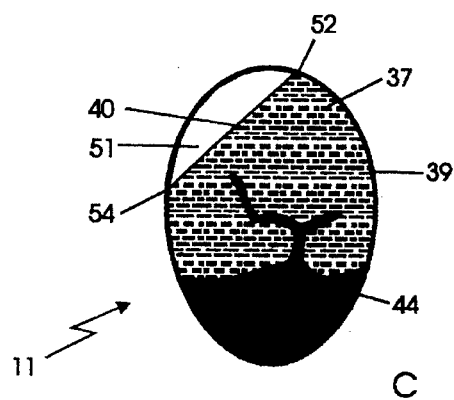
Figure 5:
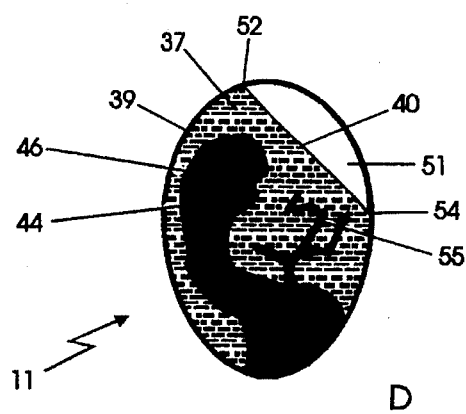
Figure 5:
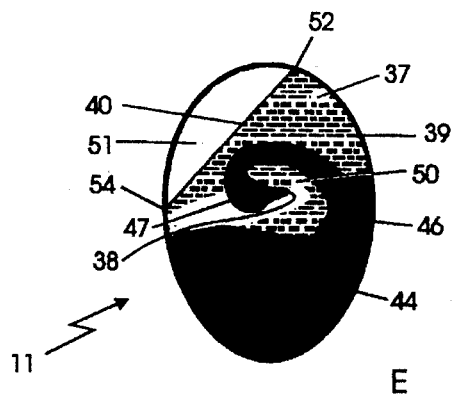
Figure 5:
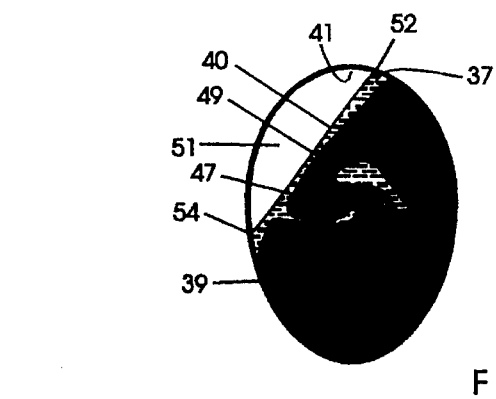
Figure 5:
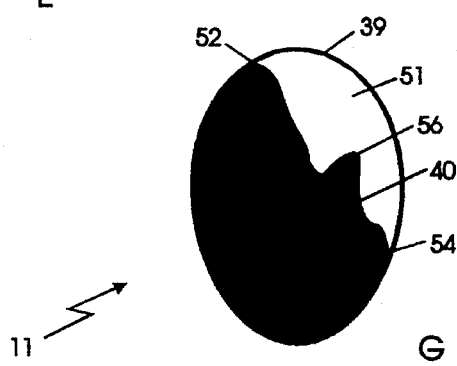

Referring now to FIG. 5, the development of embryo 44 in an object 9 such as an emu egg 11 is followed at certain intervals from shortly after laying up until internal pipping. Each of the drawings of FIG. 5 represent only one view of egg 11. FIG. 5A shows the retraction of inner membrane 40 from upper inner surface 41 of egg 11 within one or two days after laying. Usually, the location of the air sac 51 may only be determined by observing the upward tilt of egg 11 when laid on its edge for several days. The loss of weight in the area of air sac 51 will cause egg 11 to roll on outer shell 39 until air sac 51 is in an upward position.

FIG. 5B shows the initial fertilization of egg 11 which is detected as dark spot 42 at or near bottom 43 of egg 11 at 10 days. Conventionally, fertilization of egg 11 may only be determined during the incubation period by observing the weight loss of egg 11 over the first three weeks while observing the odor of egg 11 during the same period. If the weight loss is within normal limits and the smell of egg 11 is not abnormal or rotten, then egg 11 is presumed to be fertile.

FIG. 5C, taken at 15 days, shows development of blood vessels 55 in the inner membrane 40. Observation of the growth of these blood vessels 55 has heretofore only been possible by cracking outer shell 39 at the location of air sac 51, wetting inner membrane 40 and observing inner membrane 40 for blood vessels 55. This invasive procedure increases the likelihood of bacterial growth into inner membrane 40 which could migrate into embryo 44.

FIG. 5D, taken at 21 days shows the development of the embryo 44 to a stage where the shape of a new chick 46 is clearly visible. The invasive procedures outlined above for determining the development of blood vessels 55 is again conventionally used to observe the development of chick 46 from embryo 44. The hazards of the aforementioned invasive procedure are still present.

In FIG. 5E, chick 46, developing from embryo 44 after 33 days now occupies a greater portion of the volume of egg 11 within inner membrane 40. The head 47 has become clearly visible with the head 47 and beak 38 presented in outline form created when an apparent void 50 forms between the crook of the neck 49 and the bulk of the embryo 44. A yolk sac may be visible below chick 46 as it still admits the passage of light.

After 48 days, FIG. 5F shows that chick 46 is nearly fully developed and the onset of internal pipping is approaching. Inner membrane 40 has changed angle within egg 11 as lower adhesion 54 of inner membrane 40 has moved downward from its initial position shown in FIG. 5A. Lower adhesion 54 continues to move downward throughout the development of embryo 44, but the change in position becomes more pronounced between day 38 and day 50 as embryo 44 develops and becomes more active stretching inner membrane 40 and thereby pulling inner membrane 40 away from the internal surface 41 of egg 11. Upper adhesion 52 remains at or near top 53 of egg 11 throughout the development of embryo 44. Developing embryo 44 now occupies the major portion of the internal volume of egg 11 and only a narrow band of albumen 37 is visible below inner membrane 40. The specific orientation of head 47, neck 49, or legs 48 (not shown) is possible when chick 46 moves permitting an apparent void 50 between that portion and the body of chick 46 as was shown in FIG. 5E. The light readily passes through apparent void 50 showing appendages in outline.

At 50 days, FIG. 5G shows chick 46 beginning to pip or peck through at irregular surface 56 of inner membrane 40 of egg 11. At this time, egg 11 is moved to a hatching area. Use of apparatus 100 eliminates the process known as "tapping" wherein a drum stick like metallic bar is used to determine when incubated egg 11 is ready to move to the hatching chamber. Presently, the portion of shell 39 above air sac 51 of egg 11 is tapped to determine by sound whether chick 46 has pipped through inner membrane 40 and now occupies the volume of egg 11 which indicates time to move egg 11 to the hatching area. With apparatus 100, such a memos of sounding egg 11 is not necessary as it is readily apparent when chick 46 is ready to first pip through inner membrane 40.

Research may also be conducted into the probability of hatching of various shapes of eggs determining how to best hatch chicks from misshapen eggs by providing means of determining the critical parameters such as location of air sac 51 in a football or oblong egg, or the orientation of embryo 44 such that the orientation may be modified to provide embryo 44 with the best chance of survival when pipping through inner membrane 40 to gain air and finally through outer shell 39. Presently, torpedo or football shaped eggs have a very low survival rate as it is difficult to determine which end of egg 11 contains air sac 51. The method and apparatus 100 described above can readily determine the location of air sac 51 in an egg 11 as invisible light receiving means 10 views the void space created by air sac 51 as an absence of either structure or light conducting medium and therefore displays air sac 51 as a very bright area. Therefore, air sac 51 may be readily observed without respect to location.

Apparatus 100 may also be useful in determining positioning of chick 46 in large eggs where multiple embryos 44 may be present. Typically, twins in eggs have a very low survival rate. The method and apparatus 100 described above can readily determine the location of multiple fertilizations at dark spots 42 at approximately 10 days as previously set forth. The researcher or dimmer may then develop methods of enhancing the survival rate of multiple chicks 46 in a single egg 11.

Perhaps the best use of apparatus 100 will be to determine when an emu egg 11 is rotten. By observing egg 11 regularly, research into embryonic development may be carried out and a rotten egg may be detected much earlier than is conventional. It is typical for the incubation period to be carried out for about 21 days before egg 11 may be determined to be rotten as the smell of egg 11 is conventionally utilized. The method and apparatus 100 described above can readily determine the presence of a rotten egg as early as 12 days as invisible light receiving means 10 perceives a rotten egg as a cloudy image showing no structure. The rotten egg may be removed from the incubator and replaced with a new laid egg 11 earlier saving the emu farmer valuable time and money.

It has been found that a clear indication of the presence of a malpositioned chick 46 may be determined using apparatus 100 by observing upper adhesion 52 of egg 11. If upper adhesion 52 begins to recede from inner surface 41 and moves downward in a manner similar to lower adhesion 54 in the first few days of incubation, a malpositioned chick 46 will generally be found. It is expected that upon the completion of extensive embryonic research that certain embryonic enhancements may be effected utilizing apparatus 100. For instance, in addition to detecting malpositioned chicks, research may indicate that certain deformities are due to malposition of portions of the chicks body rather than a genetic defect as is currently thought. Furthermore, during embryonic development research, such known defects and their causes may be corrected by changing the diet of the mating pair and/or providing certain nutrients to embryo 44 through either invasive or non-invasive procedures. One such method is to remove a portion of outer shell 39 without rupturing inner membrane 40 and injecting the desired solution directly into embryo 44 or yolk sac. Methods of correcting deficiencies are well known in the art, but in the case of emu eggs, it is difficult to determine deficiencies without the means provided by this novel apparatus 100.

Although this apparatus 100 is primarily directed toward enhancing the development of flocks of emus through improved hatching rates of emu eggs, as outer shell 39 of egg 11 is very dark, it is obvious that the procedures outlined above could readily be utilized to effect similar changes in other bird eggs as image 25 may be fully determined with apparatus 100.

Imaging apparatus 100 may also be used in assisted hatching Presently, assisted hatches in emu eggs 11 is in itself in an embryonic stage. For instance, when a malpositioned embryo 44 is presumed to be present in an emu egg 11 because egg 11 is overdue or when it is still warm to the touch but does not properly sound as described above, the only method of determining the position of chick 46 is to crack outer shell 39 and remove a portion for access to inner membrane 40, wetting inner membrane 40 with a saline solution and observing through inner membrane 40 if beak 38 of chick 46 is in the proper position to pip through. If not, then the positioning of chick 46 must be determined by breaking through outer shell 39 in another position where the location of beak 38 is assumed based on the best guess from the first observation. Obviously, this method lends itself to potential to some loss of eggs whereas apparatus 100 may be utilized to more closely determine the position of beak 38 of chick 46 within egg 11 by observing the outline of beak 38 during movement of chick 46 as described above. The use of recording device 22 to preserve each image 25 of the structure within an object 9 becomes very important when determining position of chick 46 by observing various parts of the structure in outline form during structure movement. For instance, during the embryonic development, research may indicate that repositioning of egg 11 for a period of time may in fact, cause reorientation of chick 46 with head 47 and beak 38 oriented toward air sac 51 obviating the need for assisted hatching. Assisted hatching may further be complicated as yolk sac should be fully absorbed into body of chick 46 through the navel prior to hatching. Apparatus 100 may be used to determine the absorption of yolk sac by observing if the structure within egg 11 completely encompasses the volume contained within inner membrane 40. Timing for an assisted hatch may be determined by viewing egg 11 using apparatus 100.

Means for defining the shape of structure within object 9 may be accomplished using apparatus 100 to observe object 9 from multiple positions by viewing object 9 from more than one angle. For instance, object 9 may be viewed from three separate positions oriented at approximately 60 degrees from one another by rotating object 9 with the aid of upper end 67 of light emitting means 6. At each angle of rotation, an image 25 of object 9 may be stored upon recording device 22 and object 9 marked as to the position of viewing. Images 25 stored on recording device 22 may then be used to create a three dimensional holographic image as is well known in the art. It is also possible to digitize image 25 produced at each angle of view, create a two dimensional drawing of the image produced at each of these angles of view and, utilizing three dimensional drafting techniques, create a three dimensional drawing from the composite of multiple images 25. The three dimensional created image may then be stored on recording device 22 for future viewing and for archival purposes.

Of course, it is understood that apparatus 100 may contain more than one invisible light receiving means 10 disposed at acute angles one to another and further employing more than one viewing device 24 and or more than one recording device 22 such that an image of structure within object 9 may be observed from multiple positions as another means for defining the shape of structure within object 9. Viewing the structure from more than one angle, for instance from three separate positions oriented at approximately 60 degrees from one another, makes possible the creation of a three dimensional image utilizing holography as set forth above. It is also possible to digitize image 25 produced by each invisible light receiving means 10 as set forth above, create a two dimensional drawing of each perspective view and, utilizing three dimensional drafting techniques, create a three dimensional drawing from the composite of multiple images 25. The created image may then be stored on recording device 22 for future viewing and for archival purposes.

While the forms and methods of this invention now preferred have been illustrated and described as required by the Patent Statute, it is to be understood that other forms and methods can be utilized and still fall within the scope of the appended claims.

What we claim is:

1. In an apparatus having means for detecting the presence of internal structure in an egg, said apparatus having at least one light emitting means adapted to direct a beam of light into said egg from one side thereof, and at least one light receiving means disposed on another side of said egg remote from said light emitting means, said at least one light receiving means receiving invisible light passing through said egg, said apparatus further having means to display an image of said internal structure, the improvement wherein said light receiving means has infrared light filtration means removed therefrom.

2. An imaging apparatus as described in claim 1 wherein said at least one light receiving means comprises a charge coupled device.

3. An imaging apparatus as described in claim 2 wherein said charge coupled device is disposed in a compartment separated from a compartment containing said egg.

4. An imaging apparatus as described in claim 3 wherein compartment containing said charge coupled device is integral with said apparatus and shares a common wall with said compartment containing said egg.

5. An imaging apparatus as described in claim 2 wherein said charge coupled device is disposed in a compartment remote from said egg.

6. An imaging apparatus having means for determining the internal structure of an egg having an opaque shell, said apparatus having at least one light emitting means adapted to direct a beam of light into said egg having an opaque shell from one side thereof, and at least one light receiving means disposed on another side of said egg having an opaque shell remote from said light emitting means, said light receiving means having infrared light filtration means removed therefrom, said at least one light receiving means receiving invisible light passing through said egg having an opaque shell, said apparatus further having means to capture a visual image of said internal structure.

7. An imaging apparatus as described in claim 6 wherein said at least one light receiving means comprises a charge coupled device.

8. An imaging apparatus as described in claim 7 wherein said charge coupled device receives only infrared rays.

9. An imaging apparatus as described in claim 7 wherein said charge coupled device is disposed in a compartment separated from a compartment containing said egg.

10. An imaging apparatus as described in claim 9 wherein compartment containing said charge coupled device is integral with said apparatus and shares a common wall with said compartment containing said egg.

11. An imaging apparatus as described in claim 7 wherein said charge coupled device is disposed in a compartment remote from said egg.

12. In a method of defining the shape of structure within an egg, the egg being placed within an apparatus having at least one light emitting means adapted to direct a beam of light into the egg from one side thereof, and at least one light receiving means disposed on another side of the egg remote from said light emitting means, said at least one light receiving means receiving invisible light passing through the egg, said apparatus further having means to display an image of internal structure within the egg the improvement wherein said method comprises the steps of placing an egg having an opaque shell within said apparatus, directing said beam of light into said egg having an opaque shell (object) from one side thereof, observing a first planar image of said internal structure from a first angle of observation, rotating said egg having an opaque shell through an angle of rotation thereof to a second angle of observation, observing a second planar image of said internal structure from second angle of observation, repeatedly repeating said step of rotating said egg having an opaque shell through an angle of rotation thereof to another of a series of angles of observation, observing another of a series of multiple planar images of said internal structure from said another angle of observation and constructing composite images of the internal structure within said egg having an opaque shell using said multiple planar images.

13. The method as described in claim 12 wherein said each of said multiple planar images is stored separately within a recording device.

14. The method as described in claim 13 wherein said planar images are digitized, stored in a computer file and a composite image created as a three dimensional computerized image.

15. The method as described in claim 12 wherein said composite image comprises a three dimensional computerized image.

16. The method as described in claim 12 wherein each said angle of rotation is an acute angle.

17. The method as described in claim 16 wherein said acute angle of rotation is 60 degrees.

18. A method as described in claim 12 wherein said egg having an opaque shell is an egg of a ratite bird.

19. A method as described in claim 18 wherein said egg of a ratite bird is a cassowary egg.

20. A method as recited in claim 19 wherein said multiple planar images are viewed from three angles of observation and three planar images are utilized to construct a three dimensional image defining the shape of structure within said cassowary egg.

21. A method as described in claim 18 wherein said egg of a ratite bird is an emu egg.

22. A method as recited in claim 21 wherein said multiple planar images are viewed from three angles of observation and three planar images are utilized to construct a three dimensional image defining the shape of structure within said emu egg.

23. A method as described in claim 12 wherein said composite image is a three dimensional image constructed from the planar images observed at said first, said second and at least one of said series of another angles of observation.

24. In a method of making an imaging apparatus comprising the steps of providing an integral compartment within said apparatus, providing a door on said compartment adapted to be opened and closed, installing holding means in one side of said compartment, providing a retaining means in said holding means, providing at least one light emitting means, inserting said at least one light emitting means into said holding means allowing rotational movement therein, retaining said at least one light emitting means within said holding means with said retaining means, providing a rotatable element in another side of said compartment opposing said holding means, providing a base grommet upon said rotatable element adapted to receive an egg having an opaque shell thereon in a position between said grommet and said at least one light emitting means, said at least one light emitting means adapted to bear upon a surface of said egg opposite a surface contiguous with said grommet, providing a viewing port in another side of said compartment, providing a second compartment adjacent said first compartment having said side of said first compartment having said viewing port provided therein as a common side, providing at least one light receiving means adapted to receive invisible portions of the light spectra, disposing said at least one light receiving means in a side of said second compartment directly opposite said viewing port, said at least one light receiving means being aimed through said viewing port at a position directly above said base grommet, coupling said at least one light emitting means to a source of electrical power, said at least one light receiving means receiving invisible light passing through said egg, providing means to capture a visual image and coupling said at least one light receiving means to said means to capture a visual image, the improvement wherein said light receiving means has infrared light filtration means removed therefrom.

25. The method as described in claim 24 wherein said step of providing said at least one light receiving means comprises providing at least one charge coupled device.

26. The method as described in claim 25 wherein said step of providing said charge coupled device comprises providing a video recording device.

27. The method as described in claim 25 wherein said charge coupled device receives only infrared light emitted by said light emitting means.

28. A method of making an imaging apparatus as described in claim 25 wherein said charge coupled device is disposed in said compartment separated from said compartment containing said egg.

29. The method as described in claim 24 wherein said means to capture a visual image comprises the step of providing an electronic monitor adapted to display an image upon a visible screen.

30. The method as described in claim 28 wherein said electronic monitor is integral with said imaging apparatus.

31. The method as described in claim 29 wherein said electronic monitor is remote from said apparatus.

32. The method as described in claim 24 wherein said step of providing means to capture a visual image comprises the step of providing means to record an image.

33. In an imaging apparatus having means for detecting and defining the internal structure in an egg having an opaque shell, said apparatus having an integral enclosure, said enclosure having means to receive and support said egg having an opaque shell, at least one light emitting means adapted to direct a beam of light into said egg having an opaque shell from one side thereof, and at least one light receiving means disposed on another side of said egg having an opaque shell remote from said light emitting means, said at least one light receiving means receiving invisible light passing through said egg having an opaque shell, said apparatus further having means to capture a visual image of said internal structure the improvement wherein said light receiving means has infrared light filtration means removed therefrom.

34. An imaging apparatus as described in claim 33 wherein said at least one light receiving means comprises at least one charge coupled device.

35. An imaging apparatus as described in claim 34 wherein said charge coupled device is a video recording device.

36. An imaging apparatus as described in claim 35 wherein said video recording device has been modified by removing light emitting diodes which emit infrared light.

37. An imaging apparatus as described in claim 35 wherein said video recording device is a portable video taping device which has been modified by disabling the auto-focus lens which emits infrared light and by removing the optical coating which does not pass infrared light.

38. An imaging apparatus as described in claim 33 wherein said light receiving means is a newvicon tube.

39. An imaging apparatus as described in claim 33 wherein said light receiving means is a staticon tube.

* * * * *